United States Patent
Jooste

(10) Patent No.: US 9,504,425 B2
(45) Date of Patent: Nov. 29, 2016

(54) METHOD OF LOCATION COORDINATION VIA WIRELESS PROTOCOL BETWEEN MULTIPLE DEVICES

(71) Applicant: Verily Life Sciences LLC, Mountain View, CA (US)

(72) Inventor: Sarel Kobus Jooste, Novato, CA (US)

(73) Assignee: Verily Life Sciences LLC, Mountain View, CA (US)

(*) Notice: Subject to any disclaimer, the term of this patent is extended or adjusted under 35 U.S.C. 154(b) by 387 days.

(21) Appl. No.: 14/107,785

(22) Filed: Dec. 16, 2013

(65) Prior Publication Data

US 2015/0170504 A1    Jun. 18, 2015

(51) Int. Cl.
```
G08B 25/10      (2006.01)
A61B 5/00       (2006.01)
G08B 21/02      (2006.01)
A61B 5/0205     (2006.01)
```

(52) U.S. Cl.
CPC ........... *A61B 5/6898* (2013.01); *A61B 5/0024* (2013.01); *A61B 5/0205* (2013.01); *A61B 5/6802* (2013.01); *G08B 21/0269* (2013.01); *G08B 21/0288* (2013.01)

(58) Field of Classification Search
CPC  A61B 5/0002; A61B 5/6898; A61B 5/6802; A61B 5/0205; A61B 5/0024; G08B 21/0288; G08B 21/0269; G08B 25/10; G06F 19/3418
See application file for complete search history.

(56) References Cited

U.S. PATENT DOCUMENTS

| | | | |
|---|---|---|---|
| 7,015,817 B2* | 3/2006 | Copley | G08B 21/0283 340/539.13 |
| 7,181,505 B2 | 2/2007 | Haller | |
| 7,214,190 B1 | 5/2007 | Wilson | |
| 7,701,580 B2 | 4/2010 | Bassler et al. | |
| 7,763,856 B2 | 7/2010 | Kiesel et al. | |
| 7,817,254 B2 | 10/2010 | Hegyi et al. | |
| 7,817,276 B2 | 10/2010 | Kiesel et al. | |
| 7,844,314 B2 | 11/2010 | Al-Ali | |
| 7,894,068 B2 | 2/2011 | Bassler et al. | |
| 8,116,724 B2* | 2/2012 | Peabody | G08B 25/016 340/539.13 |

(Continued)

FOREIGN PATENT DOCUMENTS

| | | |
|---|---|---|
| EP | 1583585 | 6/2008 |
| KR | 1020110032304 A | 3/2011 |
| WO | 0158098 A2 | 8/2001 |

OTHER PUBLICATIONS

International Search Report and Written Opinion for PCT/US2014/070563 mailed Mar. 30, 2015.

(Continued)

*Primary Examiner* — An T Nguyen
(74) *Attorney, Agent, or Firm* — McDonnell Boehnen Hulbert & Berghoff LLP

(57) ABSTRACT

Systems and methods for location coordination between multiple devices are provided. In one example, a method includes receiving by a wearable device, a location signal from a positioning device having location-determining capabilities indicative of the location of the positioning device and calculating a first location of the wearable device based, at least in part, on the location of the positioning device and the strength of the location signal received by the wearable device. The wearable device may include at least one sensor configured to measure at least one physiological parameter.

12 Claims, 8 Drawing Sheets

(56) References Cited

U.S. PATENT DOCUMENTS

| | | |
|---|---|---|
| 8,153,949 B2 | 4/2012 | Kiesel et al. |
| 8,323,188 B2 | 12/2012 | Tran |
| 8,344,731 B2 | 1/2013 | Lee |
| 8,368,402 B2 | 2/2013 | Lee |
| 8,500,636 B2 | 8/2013 | Tran |
| 8,515,547 B2 | 8/2013 | Mass |
| 8,531,291 B2 | 9/2013 | Tran |
| 8,533,620 B2* | 9/2013 | Hoffman ............ A63B 24/0062 715/733 |
| 8,548,770 B2 | 10/2013 | Yuen |
| 2001/0009406 A1* | 7/2001 | Mise .................. G01S 5/0036 342/357.4 |
| 2003/0146835 A1* | 8/2003 | Carter ................ G01S 5/0036 340/539.13 |
| 2004/0259270 A1 | 12/2004 | Wolf |
| 2005/0054907 A1* | 3/2005 | Page .................. A61B 5/0095 600/316 |
| 2007/0052534 A1* | 3/2007 | Bird .................... G01S 13/878 340/539.13 |
| 2007/0255122 A1 | 11/2007 | Vol |
| 2008/0001735 A1* | 1/2008 | Tran .................. G06F 19/3418 340/539.22 |
| 2008/0004904 A1* | 1/2008 | Tran .................... A61B 5/0006 705/2 |
| 2008/0055155 A1* | 3/2008 | Hensley .............. A01K 11/008 342/357.31 |
| 2008/0319282 A1 | 12/2008 | Tran |
| 2010/0039929 A1 | 2/2010 | Cho et al. |
| 2010/0049010 A1* | 2/2010 | Goldreich ........... A61B 5/0002 600/301 |
| 2011/0028803 A1 | 2/2011 | Ollmar |
| 2011/0090081 A1* | 4/2011 | Khorashadi .......... G01S 5/0252 340/539.13 |
| 2011/0117028 A1 | 5/2011 | Zharov |
| 2011/0187547 A1* | 8/2011 | Kweon ................. B60K 35/00 340/670 |
| 2011/0210849 A1* | 9/2011 | Howard ............ G08B 13/1427 340/539.32 |
| 2012/0092156 A1* | 4/2012 | Tran .................... G06F 19/3418 340/539.12 |
| 2012/0165041 A1 | 6/2012 | Jang et al. |
| 2013/0069780 A1* | 3/2013 | Tran .................... A61B 5/0024 340/539.12 |
| 2013/0106603 A1* | 5/2013 | Weast .................. G06F 1/163 340/539.11 |
| 2013/0138716 A1* | 5/2013 | Macwan .............. G06Q 30/02 709/203 |
| 2013/0234853 A1* | 9/2013 | H. Kazerouni .... G08B 13/1427 340/572.1 |
| 2013/0265173 A1* | 10/2013 | Millar ................. G08C 17/02 340/870.07 |
| 2013/0278416 A1* | 10/2013 | Button ................. G01S 5/0072 340/539.13 |
| 2014/0167957 A1* | 6/2014 | Tsuji .................... G08B 21/24 340/539.13 |
| 2014/0197948 A1* | 7/2014 | Mo ..................... H04W 64/00 340/539.13 |
| 2014/0266731 A1* | 9/2014 | Malhotra .............. G06F 1/163 340/573.1 |
| 2015/0170504 A1* | 6/2015 | Jooste ................ A61B 5/6898 340/539.12 |

OTHER PUBLICATIONS

Machine Translation of KR 1020110032304.

Arruebo, Manuel et al., "Antibody-Conjugated Nanoparticles for Biomedical Application," Journal of Nanomaterials, vol. 2009 (2009), Article ID 439389, 24 pages (available at http://dx.doi.org/10.1155/2009/439389).

Shao, Huilin et al., "Magnetic Nanoparticles for Biomedical NMR-based Diagnostics," Beilstein Journal of Nanotechnology, 2010, 1, 142-154.

Liu, Hao-Li et al, "Magnetic Resonance Monitoring of Focused Ultrasound/Magnetic Nanoparticle Targeting Delivery of Therapeutic Agents to the Brain," PNAS Early Edition, 2010, pp. 1-6.

* cited by examiner

US 9,504,425 B2

METHOD OF LOCATION COORDINATION VIA WIRELESS PROTOCOL BETWEEN MULTIPLE DEVICES

BACKGROUND

Unless otherwise indicated herein, the materials described in this section are not prior art to the claims in this application and are not admitted to be prior art by inclusion in this section.

A body-mountable device, such as a contact lens or wrist-mounted device, can include sensors or other devices that are configured to detect one or more physiological or health-related parameters, including blood pressure, pulse rate, body temperature, glucose level, blood oxygen concentration, etc. In some cases, it may also be useful to know or track the geographical or proximate location or other contextual or environmental factors of a wearer of a body-mountable device. However, these devices may be too small, low in profile, or power sensitive to include on-board GPS or other location-tracking systems.

SUMMARY

Some embodiments of the present disclosure provide a method including: (1) receiving, by a wearable device, a location signal from a positioning device having location determining capabilities indicative of a location of the positioning device, wherein the wearable device includes at least one sensor configured to measure at least one physiological parameter; and (2) calculating, a first location of the wearable device based, at least in part, on a location of the positioning device and the strength of the location signal received by the wearable device.

Further embodiments of the present disclosure provide a wearable device including: (1) a wireless transceiver; (2) at least one sensor configured to measure at least one physiological parameter; (3) a processor; and (4) a non-transitory computer readable medium storing instructions thereon that, when executed by the processor, cause the wearable device to perform functions, the functions comprising: (i) receiving, by the wireless transceiver, a location signal from a positioning device having location determining capabilities indicative of a location of the positioning device; and (ii) calculating a first location of the wearable device based, at least in part, on the location of the positioning device and a strength of the location signal received by the wearable device.

Further embodiments of the present disclosure provide a positioning device including: (1) a wireless transceiver; (2) a location-determining system; (3) a processor; and (4) a non-transitory computer readable medium storing instructions thereon that, when executed by the processor, cause the positioning device to perform functions, the functions comprising: (i) determining a location of the positioning device using the location-determining system; and (ii) transmitting, via the transceiver, a location signal to a wearable device having at least one sensor configured to measure at least one physiological parameter, wherein the location signal is indicative of the location of the positioning device.

These as well as other aspects, advantages, and alternatives, will become apparent to those of ordinary skill in the art by reading the following detailed description, with reference where appropriate to the accompanying drawings.

DETAILED DESCRIPTION

Figure 1:
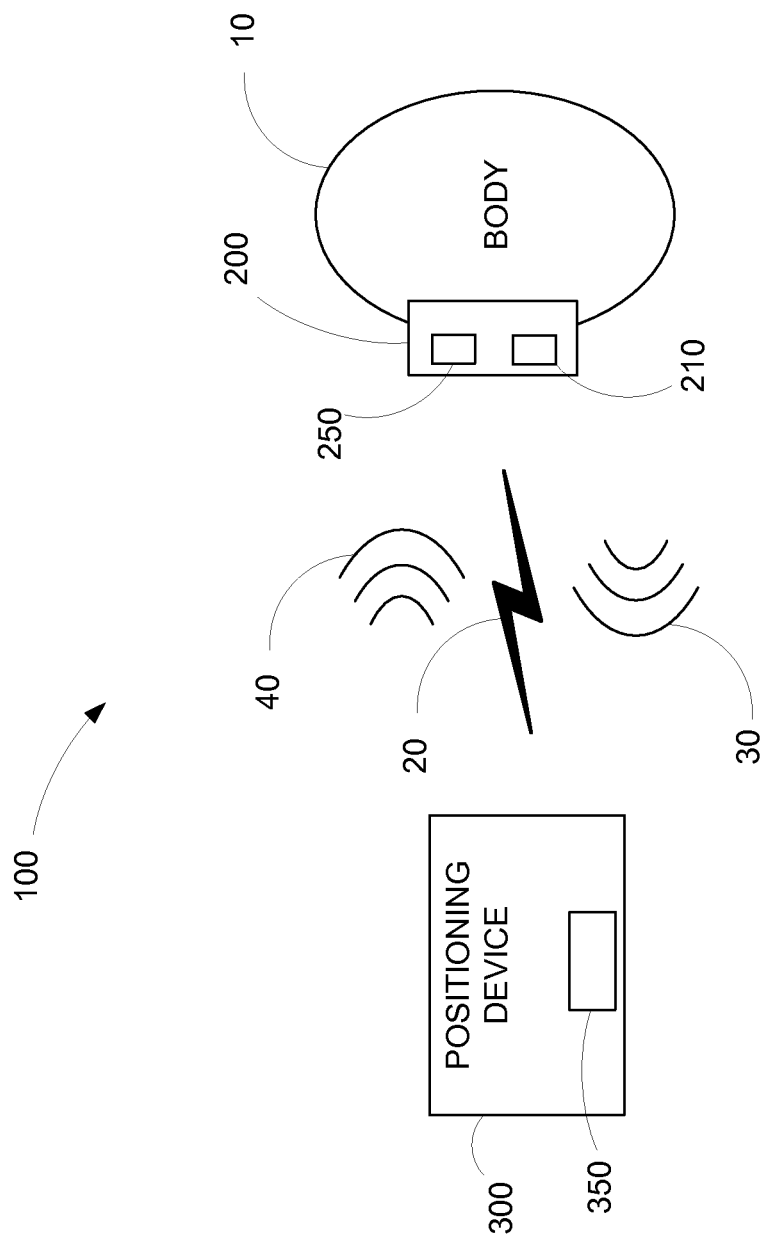
FIG. 1 is a block diagram of an example system that includes a wearable device in wireless communication with a positioning device, according to an example embodiment.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

A wearable device can detect and measure one or more physiological parameters of a person, which can include any parameters that may relate to the person's health. For example, the system may include one or more sensors for measuring blood pressure, pulse rate, respiratory rate, body temperature, skin color, perspiration, etc. Some of the physiological parameters may also be obtained by non-invasively detecting and/or measuring one or more analytes present in blood, saliva, tear fluid, or other body fluid. The one or more analytes could be any analytes that, when present in or absent from the blood or bodily fluids, or present at a particular concentration or range of concentrations, may be indicative of a medical condition or health state of the person. For example, the one or more analytes could include enzymes, reagents, hormones, proteins, viruses, bacteria, cells or other molecules, such as carbohydrates, e.g., glucose.

The term "wearable device," as used in this disclosure, refers to any device that is capable of being worn or mounted at, on, in or in proximity to a body surface, such as a wrist, ankle, waist, chest, ear, eye, head or other body part. As such, the wearable device can detect and/or measure physiological parameters while in contact with or proximate to the body. For example, the wearable device can be configured to be part of a contact lens, a wristwatch, a "head-mountable display" (HMD), an orally-mountable device such as a retainer or orthodontic braces, a headband, a pair of eyeglasses, jewelry (e.g., earrings, ring, bracelet), a head cover such as a hat or cap, a belt, an earpiece, other clothing (e.g., a scarf), and/or other devices. Further, the wearable device may be mounted directly to a portion of the body with an adhesive substrate, for example, in the form of a patch, or may be implanted in the body, such as in the skin or another organ.

Data collected by the wearable device may be used to diagnose a present medical condition in the wearer of the device, or to predict the possible occurrence of a medical condition in the future. For example, the presence, absence or level of a certain analyte in the blood of a wearer of the body-mountable device may be indicative of a medical condition or health state of the person or may be indicative that a medical event is imminent. Based on this analysis of the data, the wearer of the device may be notified and provided with a recommended course of action, for example, to take a particular medication or supplement, schedule an appointment with a medical professional, go to the hospital to seek immediate medical attention, abstain from certain activities, etc.

The term "medical condition" as used herein should be understood broadly to include any disease, illness, disorder, injury, condition or impairment—e.g., physiologic, psychological, cardiac, vascular, orthopedic, visual, speech, or hearing—or any situation affecting the health of the wearer of the device or requiring medical attention. A "medical condition" may also include a situation where a physiological parameter falls outside of a range, regimen or recommendation set by an individual, her physician, a clinician or a nutritionist. For example, a "medical condition" may be indicated when an individual consumes more than the daily recommended calories or consumes food having a high level of fat or sugars.

Additional health, contextual and environmental data may also be useful in assessing the physiological parameter data collected by the wearable device and in drawing correlations between the physical parameter data, the wearer's perceived health state and medical conditions exhibited by the wearer. Medical history and current health state information, including subjective indicia collected from the wearer of the device regarding how he or she is feeling or any symptoms he or she is experiencing, such as, "feeling cold," "feeling tired," "stressed," "feeling rested and energetic," "hard to breathe," etc. may be collected.

Further, certain environmental factors and geographical data relating to a wearer may also be collected by the system. For example, geographical location, elevation, local temperature, weather, humidity, pollution and allergen levels, whether the wearer of the device is indoors or outdoors, and whether, where or how much the wearer of the device is moving (i.e., activity level) may be gathered. Such location and environment-related data may compliment the analysis of an individual's physiological parameter data collected by a wearable device and reported health state data. This data may also be used in conjunction with physiological parameter and health-state data collected from a plurality of wearers of the devices to gain information regarding the general health state of the population, such tracking as tracking viral illness or food poisoning outbreaks in certain regions.

However, while it may be useful to collect such location, environmental and contextual information, limitations arising from the dimensions of the wearable devices, power consumption, and the nature of a device worn on a human body (i.e., ambient light sensors may not function if a wrist or ankle-mounted device is covered by clothing), present challenges to integrating GPS (or other location-tracking systems) and environmental sensors on the wearable devices themselves. Accordingly, the wearable device may be configured to receive context and location information from a positioning device having GPS functionality, such as a smartphone or GPS location beacon, communicating via a wireless protocol or the like. The positioning device may be provided as any device capable of exposing its location, including a wearable computing device such as a smartphone or tablet, a personal computer, a mobile or cellular telephone, or a satellite-based positioning device such as a GPS device or beacon. In some examples, the wearable device may be connected via a wireless protocol to a device with GPS functionality. Other location-determination technologies may also be used. The wireless protocol could be, for example, 900 Mhz RFID, Bluetooth, Bluetooth Low Energy, Wi-Fi or Zigbee. A permanent wireless connection is not required, which can benefit power consumption.

It should be understood that the above embodiments, and other embodiments described herein, are provided for explanatory purposes, and are not intended to be limiting.

II. Example System for Location Coordination Via Wireless Protocol Between Multiple Devices A system 100, including a wearable device 200 mounted to or worn on, in or in proximity to a body 10, and a positioning device 300 having location-determining capabilities is shown in FIG. 1. Program instructions 250, 350 on the wearable device 200 and positioning device 300, respectively, can operate to determine an indication of the position of the wearable device 200 based, at least in part, on the position of the positioning device 300. A device's "position" could be any location with respect to a 2-dimensional or 3-dimensional coordinate system (e.g., a location with respect to X, Y and Z axes) or with respect to a cartographic location description (e.g., a street address), and may further include a global position (e.g., latitude, longitude and elevation), a hyper-local position (such as a location within a home or building), and/or any position at any level of resolution therebetween. The wearable device 200 and the positioning device are in communication via a wireless communication network. The wearable device 200, having a sensor 210, may be configured to detect, quantify, and/or monitor one or more physiological parameters of a person wearing device 200.

Figure 2:
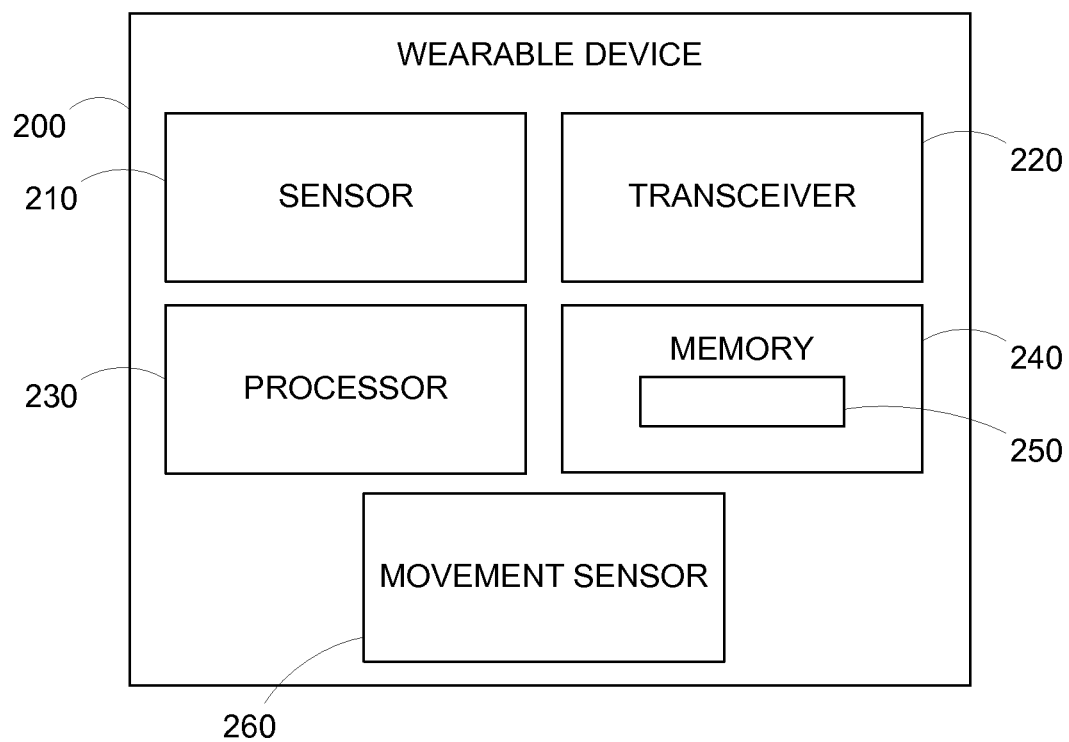
FIG. 2 is a block diagram of an example wearable device, according to an example embodiment.

Turning to FIG. 2, the wearable device may include one or more sensors 210, an wireless transceiver 220, a processor 230 and a memory 240. The sensor 210, which may also include a power supply and a controller (not shown), may include any sensor for measuring a physiological parameter, including, but not limited to, one or more of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor. The power supply may be configured to harvest ambient energy to power the sensor 200, for example, by harvesting incident radio frequency radiation with an antenna. Other energy harvesting systems, such as cells adapted to capture energy from incoming ultraviolet, visible, and/or infrared radiation or an inertial power scavenging system for capturing energy from ambient vibrations or movements, can additionally or alternatively be included. The device 200 can also be self-powering, such as by movement, compression or electrochemically. Wireless transceiver 220 can be any type of device, including a dual-purpose antenna that is capable of sending and receiving information from a remote source, such as a positioning device 300.

Example processor(s) 230 include, but are not limited to, CPUs, Graphics Processing Units (GPUs), digital signal processors (DSPs), application specific integrated circuits (ASICs). Memory 240 is a non-transitory computer-readable medium that can include, without limitation, magnetic disks, optical disks, organic memory, and/or any other volatile (e.g. RAM) or non-volatile (e.g. ROM) storage system readable by the processor 230. The memory 240 can include a data storage to store indications of data, such as sensor readings, program settings (e.g., to adjust behavior of the wearable device 200), user inputs (e.g., from a user interface on the device 200 or communicated from a remote device), one or more baseline profiles, etc. The memory 240 can also include program instructions 250 for execution by the processor 230 to cause the device 200 to perform processes specified by the instructions 250.

Figure 3:
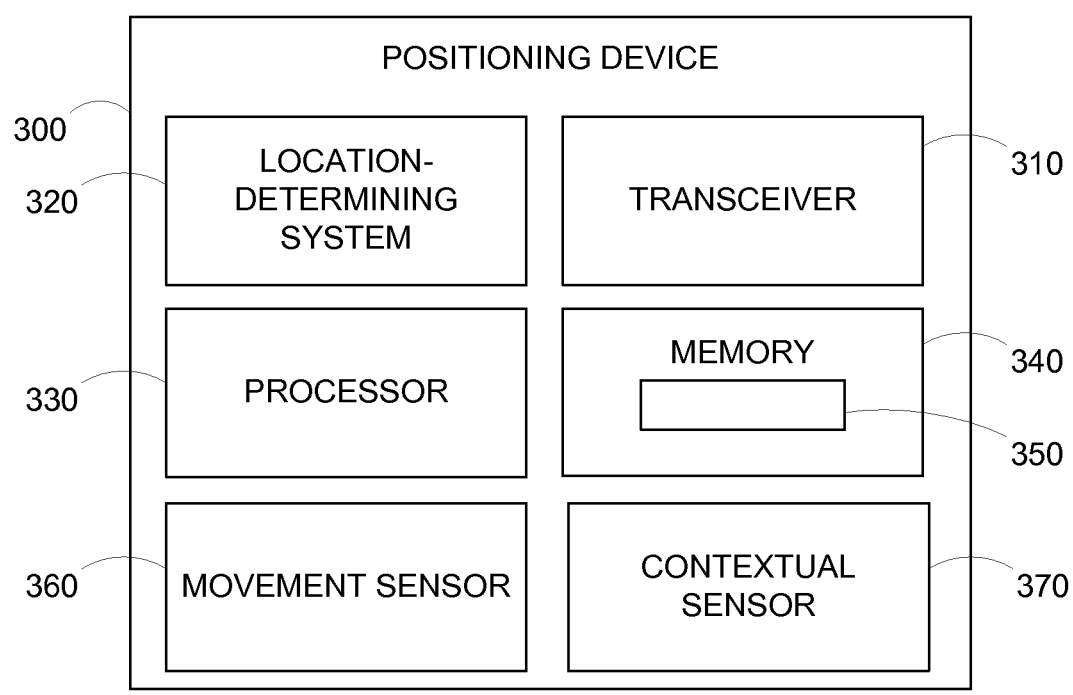
FIG. 3 is a block diagram of an example positioning device, according to an example embodiment.

A schematic representation of an example positioning device 300 is shown in FIG. 3. The positioning device 300 may include a wireless transceiver 310, a location-determining system 320, a processor 330 and memory 340. Location determining system 320 may be any location tracking, location determining or navigation system, including global satellite positioning systems (such as GPS, NAVSAT, Galileo, GLONASS, and COMPASS), regional navigation systems (such as BeiDou, IRNSS, and QZSS), inertial navigation systems, a wireless mesh network, cellular or mobile phone network, locator or positioning beacons, etc. Program instructions 350 for execution by the processor 330 may be stored in the memory 340, which may include any non-transitory computer-readable medium such as, without limitation, magnetic disks, optical disks, organic memory, and/or any other volatile (e.g. RAM) or non-volatile (e.g. ROM) storage system readable by the processor 330. The memory 340 can also include a data storage to store position data, program settings (e.g., to adjust behavior of the positioning device 300), and user inputs (e.g., from a user interface on the device 300 or communicated from a remote device). Processor 330 may be provided as any of the embodiments described above with respect to the processor 230 of the wearable device 200.

In operation, the wearable device 200 may detect or be notified when the wearable device 200 is within range of the positioning device 300. The wearable device 200 may send, via wireless transceiver 220, and the positioning device 300 may receive, via the wireless transceiver 310, a request 30, such as a connection request. The program instructions 250 stored in memory 240 can cause the wearable device 200 to establish a wireless connection 20 between the wearable device 200 and the positioning device 300. In some embodiments, wearable device 200 and positioning device 300 can communicate using hardware and/or software operating according to one or more wireless standards or protocols, such as, but not limited to, RFID, Bluetooth, Wi-Fi, ZigBee, WiMax, or a Wireless Wide Area Network (e.g., TDMA, CDMA, GSM, UMTS, EV-DO, LTE), etc. In other embodiments, wearable device 200 and positioning device 300 can communicate by one or more wired protocols such as, but not limited to, a Universal Serial Bus protocol, a Registered Jack protocol (e.g., RJ-25), or a wired Local Area Network protocol (e.g., Ethernet). In examples where an RFID protocol is used, the RF Field detect functionality of the RFID controller may be triggered when a RFID transmitter in the positioning device 300 is turned on and the wearable device 200 is present in the RF field. Where a Bluetooth protocol is used, the program instructions 250 on the wearable device 200 may be triggered when the wearable device is already paired with the positioning device 300, and the Bluetooth hardware notifies both devices that they are within range. In the event of unpaired devices, the Bluetooth discovery feature may trigger the program instructions. Bluetooth low energy uses a similar principle as Bluetooth, but with power optimization.

When a connection 20 is made between the wearable 200 and positioning 300 devices, program instructions 350 cause the location determining system 320 of the positioning device 300 to determine its location, such as its GPS location. The positioning device 300 may then transmit a location signal 40 to the wearable device 200 indicative of the location of the positioning device 300. In other examples, positioning device 300 may automatically emit its location, similar to a beacon, without necessarily establishing a connection with the wearable device 200. Upon receiving the location signal 40, program instructions 250 may cause the wearable device to calculate its location based, at least in part, on the location of the positioning device 300 and the strength of the location signal 40 received by the wearable device 200. If data is reported from the wearable device to the internet/cloud by way of proxying through the positioning device 300 (i.e., the positioning device 300 also acts as a reader for the wearable device 200), the location of the wearable device 200 can be cached on the positioning device 300 and the wearable device 200 does not need to store an indication of its location.

If the wearable device 200 is proximate to the positioning device 300, then the location of the wearable device may be assigned to that of the positioning device. For example, if the positioning device 300 is implemented as a smart phone, the user of the wearable device 200 may have both the wearable device 200 and the positioning device 300 on or in close proximity to her person (i.e., the wearable device 200 on her wrist and the positioning device 200 in her pocket or a handbag). In such cases, the position of the wearable device 200 and the positioning device 300 are essentially the same. However, in some instances, the wearable device 200 and positioning device 300 will not be in the same approximate location. In embodiments utilizing wireless protocols that cover longer distances (such as Wi-Fi), the strength of the location signal 40 can be used to adjust the location that is assigned to the wearable device 200. If the wireless transceiver 310 of the positioning device 300 is directional, the location of the wearable device 200 can also be determined based, at least in part, on the direction of the signal 40.

The program instructions 250 may also be configured to reestablish a connection between the two devices if the connection 20 is broken and determine or estimate the location of the wearable device 200 during the period of disconnect. In response to termination of the wireless connection 20 between the wearable device 200 and the positioning device 300, the program instructions 250 may further cause the wearable device 200 to store its current location (as determined from the location signal 40). If the wearable device 200 includes one or more movement sensors 260, the program instructions 250 may cause the wearable device 200 to store movement data indicative of movement of the wearable device 200. Movement data may be used to determine how far the wearable device 200 has moved away from the positioning device 300 (e.g., number of steps taken, etc.). The one or more movement sensors may include one or more of a compass, an accelerometer, an inertial measurement unit (IMU), an altitude meter and a gyroscope. Movement data may be any of direction, altitude, speed and acceleration. For example, if one of the one or more movement sensors 260 includes an altitude meter, then the stored movement data can also include an elevation increase or decrease. If one of the one or more movement sensors 260 includes a compass, then the stored movement data can also include the direction of the wearable device's movement. The movement data may also include a timestamp. A clock or relative clock on the wearable device 200 may be used to timestamp distance, direction or elevation movement data recorded on the wearable device.

When a connection 20 is reestablished, a new position can be calculated for the wearable device 200. The wearable device 200 may receive an updated location signal 20 from the positioning device 200, including a timestamp, indicative of the current position of the positioning device 300. For example, network time from the positioning device 300 (e.g., based on at least periodic connection of the position device 300 to the Internet, to a cellular wireless network, or other network) may be used to timestamp location data of the positioning device 300. Program instructions 250 stored in the memory 240 may cause the wearable device 200 to correlate the wearable device movement data and the positioning device updated location signal based, at least in part, on their respective timestamps.

During a period of disconnect, at least four types of movement may occur: (1) neither device moves, (2) both devices move, (3) only the wearable device moves, and (4) only the positioning device moves. Accordingly, the recorded positions of both devices 200, 300 prior to disconnect, an updated location of the positioning device 300 after disconnect, and data indicative of movement of the wearable device 200 and/or positioning device 300 may be relevant to determining a new position for the wearable device. The updated location of the wearable device 200 may be calculated based, at least in part, on the correlated wearable device movement data and the positioning device updated location signal, the strength of the updated location signal received by the wearable device, and the first location of the wearable device. The relative offset between the devices on the XYZ planes can be calculated to derive the relative interpolated position of the wearable device.

If the positioning device 300 was stationary during the time of disconnect, the new location of the wearable device 200 may be determined as described above based, at least in part, on the strength of the location signal 40 and, in some embodiments, the direction of the location signal 40. The wearable device movement data may also be taken into account when calculating the wearable device's updated position. If, however, the positioning device 300 moves during the period of disconnect between the two devices, an updated location of the positioning device 300 can be recorded in order to determine relative movement between the wearable device 200 and the positioning device 300. For example, where both devices have moved during the period of disconnect, it may be useful to know how far they have moved towards or away from one another, in calculating an updated position of the wearable device 200.

In some examples, the system may operate without the wearable device 200 and/or positioning device 300 sending a connection request 30 or without necessarily establishing a wireless connection 20 between the devices. For example, the positioning device 300 may be configured to emit a location signal 40, without a request by a wearable device 200 or without establishing a wireless connection, such as in the case of a beacon. The position of the wearable device 200 may be determined as described above. Where the wearable device 200 loses the location signal 40 of the positioning device 300 because, for example, the wearable device 200 moves out of range or the positioning device 300 terminates the location signal 40, the wearable device 200 will store its current location (as determined from the location signal 40) and the same steps described above can be followed.

The system 100 may also employ multiple positioning devices 300 to determine the position of the wearable device 200, either consecutively or simultaneously. For example, a wearable device 200 may receive a location signal 40 from a first positioning device 300 while in a first location and may subsequently receive a location signal 40 from a second positioning device 300 as it moves to a second location. Additionally or alternatively, a wearable device 200 may receive location signals 40 from one or more positioning devices 300 at the same time. As described above, the wearable device 200 may use, among other things, the strength and/or direction of the location signals 40 received from the one or more positioning devices 300 to determine its position. In some aspects, the use of more than one positioning device 300 may provide a better estimate of the location of the wearable device 200, which may be determined by averaging the data between the positioning devices 300, triangulation, and other techniques.

As a power-saving technique, the location-determining system 320 on the positioning device 300 may be activated and an updated location of the positioning device determined only if activity is present. Activity may be sensed by one or more movement sensors 360 on the positioning device 300. Movement sensor(s) 360 may include one or more of an accelerometer, an inertial measurement unit, an altitude meter and a gyroscope. In examples where the positioning device 300 is a smartphone, the device's accelerometer or IMU may be used to sense activity. The frequency of location determination may be relative to the level of activity sensed by the accelerometer or IMU. For example, less activity may result in less frequent location polling by the positioning device 300.

In the event that the wireless connection or wireless hardware between the two devices is incapable of notifying the devices of connection or disconnection, proximity of the devices may also be determined. The wearable device 200 or positioning device 300 may send out a periodic echo or connection request. If a response is received from the wearable device 220 or positioning device, or vice versa, the devices can determine that they are within range. Signal strength or the time delay in receiving the response can be used to determine the distance between the devices. To reduce power consumption, the delay between periodic echo or connection requests can be exponentially increased up to a preset limit. For example, an echo at one second could be followed by an echo two seconds later, and so on up to a 30 second delay. The first echo or connection request that does not receive a response returns the delay time between echo or connection requests back to one second. To prevent location data from being lost in the period between echoes (e.g. 30 seconds), if the wearable device moved out of range of the positioning device, the wearable device 200 and the positioning device 300 can each record their location and/or movement data in between consecutive echo or connection requests, in anticipation of a disconnect between the two devices.

In some examples, the location signal 40 may further contain contextual information, such as, whether the positioning device is indoors or outdoors, ambient light intensity, weather information, etc. Accordingly, the positioning device 300 may further include one or more contextual sensors 370, which may include any sensors for providing information regarding the state or environment of the positioning device 300, including light sensors, humidity sensors, pressure sensors, thermometers, etc.

The processing steps described above may, alternatively, be carried out by a processor located on the positioning device or another remote computing device. For example, the wearable device 200 may send an echo signal to the positioning device 300 and the positioning device may determine the location of the wearable device based, at least in part, on the position of the positioning device 300, and one or more of the strength and direction of the echo signal received from the wearable device 200. In instances where a disconnect of the connection between the two devices occurs, the wearable device 200 may send movement data, indicative of movement of the wearable device, to the positioning device 300 for calculation of an updated position of the wearable device 300.

Further, some embodiments of the system and/or wearable devices may include privacy controls which may be automatically implemented or controlled by the wearer of the device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

The wearable device 200 may be configured to transmit data, such as collected physiological parameter data, location and contextual data, and data regarding the wearer's health state, via a communication interface over one or more communication networks to a remote server. The communication interface may include any means for the transfer of data, including both wired and wireless communications, include a universal serial bus (USB) interface, a secure digital (SD) card interface, a plain old telephone service (POTS) network, a cellular network, a fiber network and a data network. In one embodiment, the communication interface includes a wireless transceiver for sending and receiving communications to and from the server. The server may include any type of remote computing device or remote cloud computing network. Further, communication network may include one or more intermediaries, including, for example wherein the wearable device transmits data to a mobile phone or other personal computing device, which in turn transmits the data to the server.

In addition to receiving communications from the wearable device 200 and/or positioning device 300, such as collected physiological parameter data, location and contextual data, and data regarding health state as input by the user, the server may also be configured to gather and/or receive either from the wearable device 200 or from some other source, information regarding a wearer's overall medical history, environmental factors and geographical data. For example, a user account may be established on the server for every wearer that contains the wearer's medical history. Moreover, in some examples, the server may be configured to regularly receive information from sources of environmental data, such as viral illness or food poisoning outbreak data from the Centers for Disease Control (CDC) and weather, pollution and allergen data from the National Weather Service. Further, the server may be configured to receive data regarding a wearer's health state from a hospital or physician. Such information may be used in the server's decision-making process, such as recognizing correlations and in generating clinical protocols.

Correlations may be derived between the analyte concentration(s) measured by the system, the health state reported by the patient and all other information received by the server or remote computing device. For example, analysis of the analyte data and the health state data may reveal that the patient has experienced certain adverse health conditions, such as a migraine or a heart attack, when an analyte reaches a certain concentration. This correlation data may be used to generate recommendations for the patient, or to develop a clinical protocol. Blood analysis may be complemented with other physiological measurements such as blood pressure, heart rate, body temperature etc., and location and contextual data, in order to add to or enhance these correlations. For example, the analysis of the analyte data measured by the wearable device 200 and the location of the wearable device (as coordinated from the positioning device 300) may reveal that the wearer of the device experiences certain adverse health conditions, such as allergic reaction, when present in a certain geographical region. Further, date, time of day and geographical location data may be used to detect and monitor spatial and temporal spreading of diseases.

The server may also be configured to make determinations regarding the efficacy of a drug or other treatment based on information regarding the drugs or other treatments received by a wearer of the device and, at least in part, the physiological parameter data and the indicated health state of the user. From this information, the server may be configured to derive an indication of the effectiveness of the drug or treatment. For example, if a drug is intended to treat nausea and the wearer of the device does not indicate that he or she is experiencing nausea after beginning a course of treatment with the drug, the server may be configured to derive an indication that the drug is effective for that wearer. In another example, a wearable device may be configured to measure blood glucose. If a wearer is prescribed a drug intended to treat diabetes, but the server receives data from the wearable device indicating that the wearer's blood glucose has been increasing over a certain number of measurement periods, the server may be configured to derive an indication that the drug is not effective for its intended purpose for this wearer.

III. Example Methods

Figure 4:
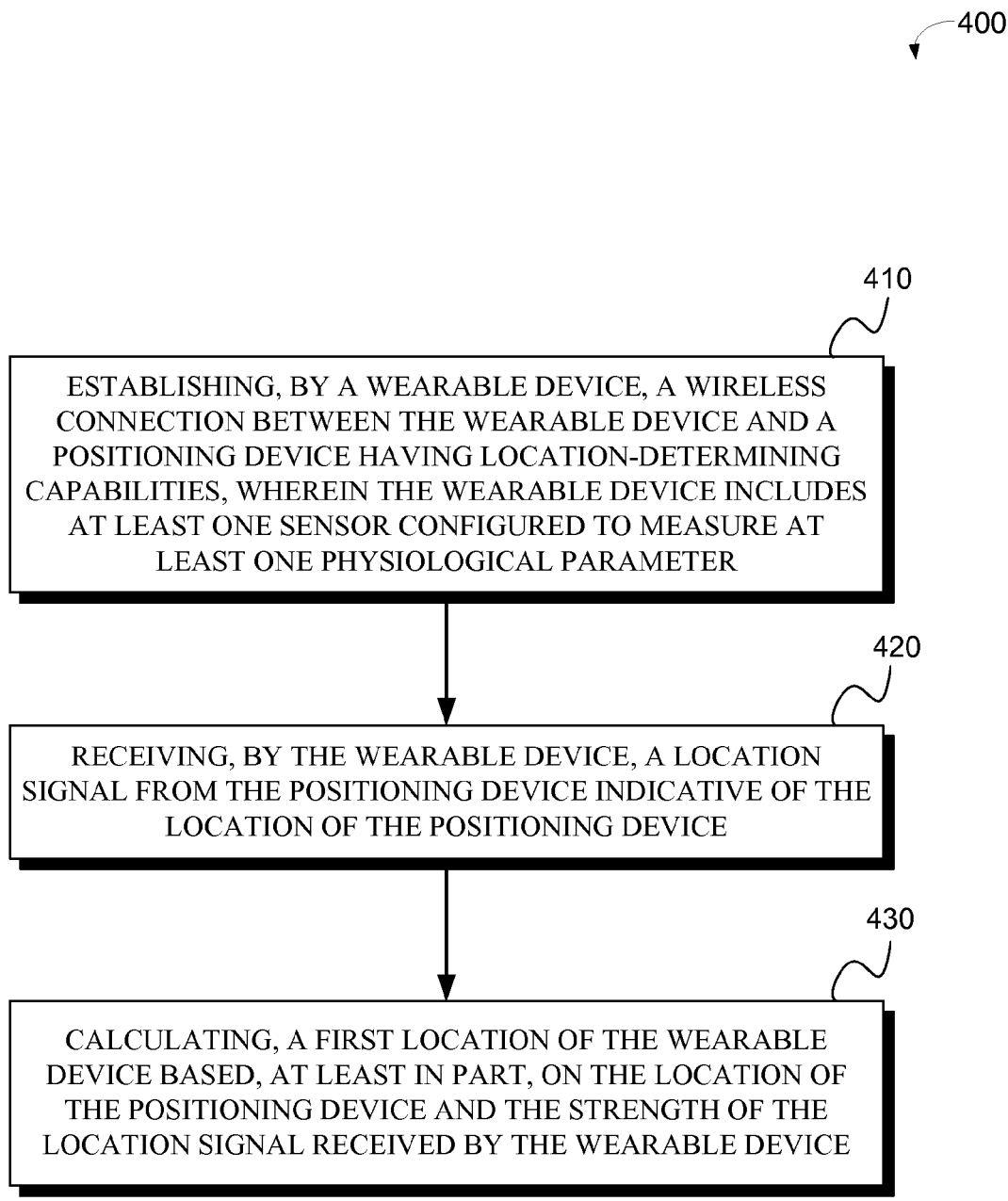
FIG. 4 is a flow chart of an example method, according to an example embodiment.

FIG. 4 is a flowchart of a method 400 for location coordination between multiple devices. In a first step, a wearable device establishes a wireless connection between the wearable device and a positioning device having location-determining capabilities (410). The wearable device includes at least one sensor configured to measure at least one physiological parameter. The wearable device receives location signal from the positioning device indicative of the location of the positioning device (420) and calculates a first location based, at least in part, on the location of the positioning device and the strength of the location signal received by the wearable device (430). The first location of the wearable device may further be calculated based, at least in part, on the direction of the location signal received by the wearable device. In some examples, the wireless transceiver of the positioning device may be directional.

In response to termination of the wireless connection between the wearable device and the positioning device, the method may further include storing the first location of the wearable device; and storing movement data, which may include a timestamp, received from one or more movement sensors on the wearable device indicative of movement of the wearable device. The one or more movement sensors on the wearable device may include one or more of a compass, an accelerometer, an inertial measurement unit, an altitude meter, and a gyroscope. The wearable device movement data may include one or more of direction, altitude, speed, and acceleration. The wearable device may also detect whether it is within range of the positioning device.

In response to reestablishing a wireless connection between the wearable device and the positioning device, the wearable device may receive an updated location signal from the positioning device indicative of one or more updated locations of the positioning device, said updated location signal further including a timestamp. The wearable device movement data and the positioning device updated location signal may be correlated based, at least in part, on their respective timestamps. An updated location of the wearable device may then be calculated based, at least in part, on the correlated wearable device movement data and the positioning device updated location signal, the strength of the updated location signal received by the wearable device, and the first location of the wearable device. The updated location of the wearable device may further be calculated based, at least in part, on movement data received from the positioning device indicative of movement of the positioning device.

IV. Example Wearable Devices

Various examples of wearable devices 200 for use in the above described systems and methods are illustrated in FIGS. 5A-5B, 6, 7A-7B, and 8A-8B.

A. Example Eye Mountable Device

Figure 5A:
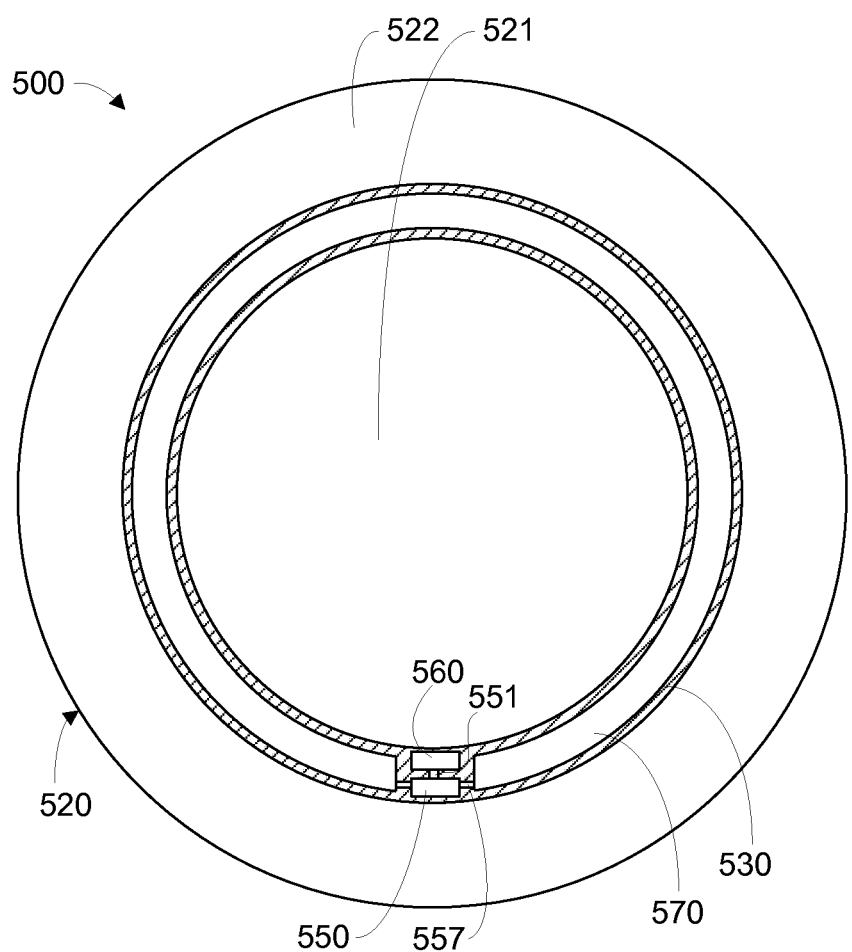
FIG. 5A is a bottom view of an example eye-mountable device, according to an example embodiment.
Figure 5B:
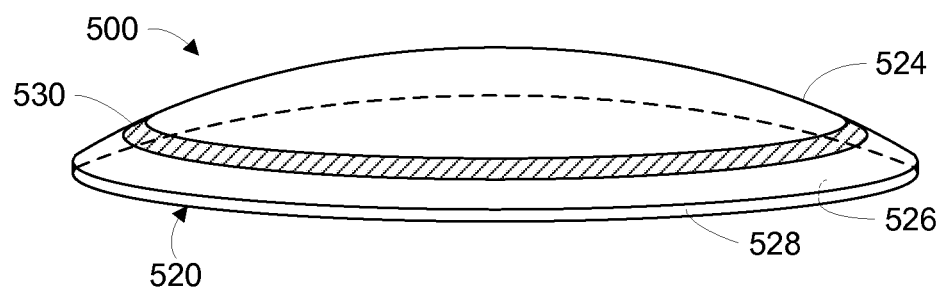
FIG. 5B is a side view of the example eye-mountable device shown in FIG. 5A, according to an example embodiment.

In one example, wearable device 200 may be provided as an eye-mountable device 500, as shown in FIGS. 5A and 5B. FIG. 5A is a bottom view of an example eye-mountable electronic device 500 (or ophthalmic electronics platform). FIG. 5B is an aspect view of the example eye-mountable electronic device shown in FIG. 5A. It is noted that relative dimensions in FIGS. 5A and 5B are not necessarily to scale, but have been rendered for purposes of explanation only in describing the arrangement of the example eye-mountable electronic device 500. The polymeric material 520 can be a substantially transparent material to allow incident light to be transmitted to the eye while the eye-mountable device 500 is mounted to the eye. The polymeric material 520 can be a biocompatible material similar to those employed to form vision correction and/or cosmetic contact lenses in optometry, such as polyethylene terephthalate ("PET"), polymethyl methacrylate ("PMMA"), polyhydroxyethylmethacrylate ("polyHEMA"), silicone hydrogels, combinations of these, etc. The polymeric material 520 can be formed with one side having a concave surface 526 suitable to fit over a corneal surface of an eye. The opposite side of the disk can have a convex surface 524 that does not interfere with eyelid motion while the eye-mountable device 500 is mounted to the eye. A circular outer side edge 528 connects the concave surface 524 and convex surface 526.

The eye-mountable device 500 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of the eye-mountable device 500 can be selected according to the size and/or shape of the corneal surface of the wearer's eye. While the eye-mountable device 500 is mounted in an eye, the convex surface 524 faces outward to the ambient environment while the concave surface 526 faces inward, toward the corneal surface. The convex surface 524 can therefore be considered an outer, top surface of the eye-mountable device 500 whereas the concave surface 526 can be considered an inner, bottom surface. The "bottom" view shown in FIG. 5A is facing the concave surface 526. From the bottom view shown in FIG. 5A, the outer periphery 522, near the outer circumference of the curved disk is curved to extend out of the page, whereas the central region 521, near the center of the disk is curved to extend into the page.

A substrate 530 is embedded in the polymeric material 520. The substrate 530 can be embedded to be situated along the outer periphery 522 of the polymeric material 520, away from the central region 521. The substrate 530 does not interfere with vision because it is too close to the eye to be in focus and is positioned away from the central region 521 where incident light is transmitted to the eye-sensing portions of the eye. Moreover, the substrate 530 can be formed of a transparent material to further mitigate effects on visual perception.

The substrate 530 can be shaped as a circular ring (e.g., a disk with a centered hole). The flat surface of the substrate 530 (e.g., along the radial width) is a platform for mounting electronics such as chips (e.g., via flip-chip mounting) and for patterning conductive materials (e.g., via microfabrication techniques such as photolithography, deposition, plating, etc.) to form electrodes, antenna(e), and/or interconnections. The substrate 530 and the polymeric material 520 can be approximately cylindrically symmetric about a common central axis. The substrate 530 can have, for example, a diameter of about 10 millimeters, a radial width of about 1 millimeter (e.g., an outer radius 1 millimeter greater than an inner radius), and a thickness of about 50 micrometers. However, these dimensions are provided for example purposes only, and in no way limit the present disclosure. The substrate 530 can be implemented in a variety of different form factors.

Controller 550, bio-interactive electronics 560, and a wireless transceiver, such as loop antenna 570, are disposed on the embedded substrate 530. The controller 550 can be a chip including logic elements configured to operate the bio-interactive electronics 560 and the loop antenna 570. The controller 550 is electrically connected to the loop antenna 570 by interconnects 557 also situated on the substrate 530. Similarly, the controller 550 is electrically connected to the bio-interactive electronics 560 by an interconnect 551. The interconnects 551, 557, the loop antenna 570, and any conductive electrodes (e.g., for an electrochemical analyte bio-sensor, etc.) can be formed from conductive materials patterned on the substrate 530 by a process for precisely patterning such materials, such as deposition, photolithography, etc. The conductive materials patterned on the substrate 530 can be, for example, gold, platinum, palladium, titanium, carbon, aluminum, copper, silver, silver-chloride, conductors formed from noble materials, metals, combinations of these, etc.

As shown in FIG. 5A, which is a view facing the convex surface 524 of the eye-mountable device 500, bio-interactive electronics 560 is mounted to a side of the substrate 530 facing the convex surface 524. Where the bio-interactive electronics 560 includes an analyte bio-sensor, for example, mounting such a bio-sensor on the substrate 530 facing the convex surface 524 allows the bio-sensor to sense analyte concentrations in tear film through a channel in the polymeric material 520 to convex surface 524. In some embodiments, some electronic components can be mounted on one side of the substrate 530, while other electronic components are mounted to the opposing side, and connections between the two can be made through conductive materials passing through the substrate 530.

In one example, the controller 550 includes a sensor interface module that is configured to operate an analyte bio-sensor. The analyte bio-sensor can be, for example, an amperometric electrochemical sensor that includes a working electrode and a reference electrode. A voltage can be applied between the working and reference electrodes to cause an analyte to undergo an electrochemical reaction (e.g., a reduction and/or oxidation reaction) at the working electrode. The electrochemical reaction can generate an amperometric current that can be measured through the working electrode. The amperometric current can be dependent on the analyte concentration. Thus, the amount of the amperometric current that is measured through the working electrode can provide an indication of analyte concentration. In some embodiments, the sensor interface module can be a potentiostat configured to apply a voltage difference between working and reference electrodes while measuring a current through the working electrode.

B. Example Wrist-Mountable Device

Figure 6:
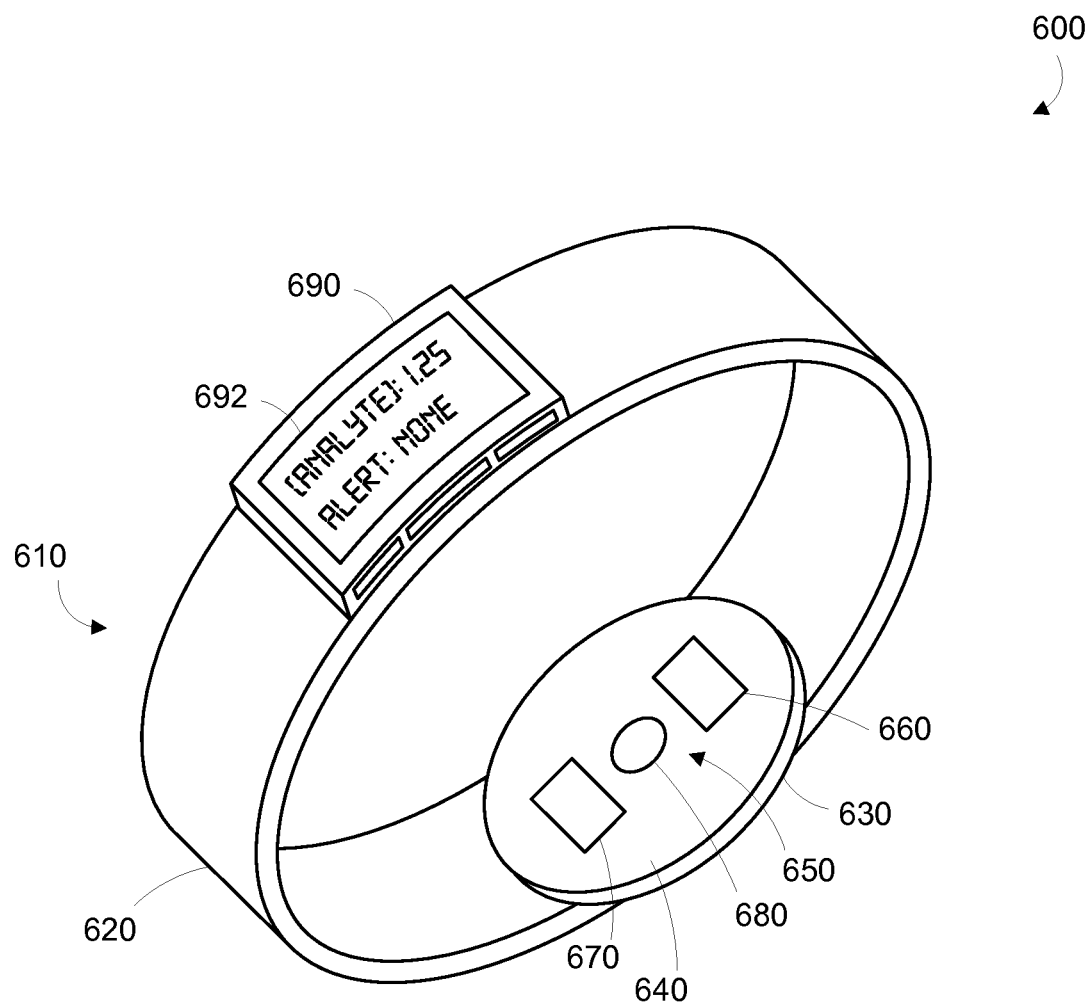
FIG. 6 illustrates an example wrist-mountable device, according to an example embodiment.

In another example, wearable device 200 may be provided as a wrist-mountable device 600, as shown in FIG. 6. The wrist-mountable device 600 can automatically measure a plurality of physiological parameters of a person wearing the device. The device 600 is also capable of being worn at, on or in proximity to, an ankle, waist, chest, or other body part. The device may be placed in close proximity to the skin or tissue, but need not be touching or in intimate contact therewith. A mount 610, such as a belt, wristband, ankle band, etc. can be provided to mount the device at, on or in proximity to the body surface. The mount 610 may prevent the wearable device from moving relative to the body to reduce measurement error and noise. In one example, shown in FIG. 6, the mount 610, may take the form of a strap or band 620 that can be worn around a part of the body. Further, the mount 610 may be an adhesive substrate for adhering the wearable device 600 to the body of a wearer.

A measurement platform 630 is disposed on the mount 610 such that it can be positioned on the body where subsurface vasculature is easily observable. An inner face 640 of the measurement platform is intended to be mounted facing to the body surface. The measurement platform 630 may house the data collection system 650, which may include at least one detector 660 for detecting at least one physiological parameter, which could include any parameters that may relate to the health of the person wearing the wearable device. For example, the detector 660 could be configured to measure blood pressure, pulse rate, respiration rate, skin temperature, etc. At least one of the detectors 660 is configured to non-invasively measure one or more analytes in blood circulating in subsurface vasculature proximate to the wearable device. In a non-exhaustive list, detector 660 may include any one of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor. The components of the data collection system 650 may be miniaturized so that the wearable device may be worn on the body without significantly interfering with the wearer's usual activities.

In some examples, the data collection system 650 further includes a signal source 670 for transmitting an interrogating signal that can penetrate the wearer's skin into the portion of subsurface vasculature, for example, into a lumen of the subsurface vasculature. The interrogating signal can be any kind of signal that is benign to the wearer, such as electromagnetic, magnetic, optic, acoustic, thermal, mechanical, and results in a response signal that can be used to measure a physiological parameter or, more particularly, that can detect the binding of the clinically-relevant analyte to the functionalized particles. In one example, the interrogating signal is an electromagnetic pulse (e.g., a radio frequency (RF) pulse) and the response signal is a magnetic resonance signal, such as nuclear magnetic resonance (NMR). In another example, the interrogating signal is a time-varying magnetic field, and the response signal is an externally-detectable physical motion due to the time-varying magnetic field. The time-varying magnetic field modulates the particles by physical motion in a manner different from the background, making them easier to detect. In a further example, the interrogating signal is an electromagnetic radiation signal. In particular, the interrogating signal may be electromagnetic radiation having a wavelength between about 400 nanometers and about 1600 nanometers. The interrogating signal may, more particularly, comprise electromagnetic radiation having a wavelength between about 500 nanometers and about 1000 nanometers. In some examples, the functionalized particles include a fluorophore. The interrogating signal may therefore be an electromagnetic radiation signal with a wavelength that can excite the fluorophore and penetrate the skin or other tissue and subsurface vasculature (e.g., a wavelength in the range of about 500 to about 1000 nanometers), and the response signal is fluorescence radiation from the fluorophore that can penetrate the subsurface vasculature and tissue to reach the detector.

In some cases, an interrogating signal is not necessary to measure one or more of the physiological parameters and, therefore, the wearable device 600 may not include a signal source 670. For example, the functionalized particles include an autofluorescent or luminescent marker, such as a fluorophore, that will automatically emit a response signal indicative of the binding of the clinically-relevant analyte to the functionalized particles, without the need for an interrogating signal or other external stimulus. In some examples, the functionalized particles may include a chemiluminescent marker configured to produce a response signal in the form of luminescence radiation produced in response to a chemical reaction initiated, at least in part, to the binding of the target analyte to the particle.

A collection magnet 680 may also be included in the data collection system 650. In such embodiments, the functionalized particles may also be made of or be functionalized with magnetic materials, such as ferromagnetic, paramagnetic, super-paramagnetic, or any other material that responds to a magnetic field. The collection magnet 680 is configured to direct a magnetic field into the portion of subsurface vasculature that is sufficient to cause functionalized magnetic particles to collect in a lumen of that portion of subsurface vasculature. The magnet may be an electromagnet that may be turned on during measurement periods and turned off when a measurement period is complete so as to allow the magnetic particles to disperse through the vasculature.

The wearable device 600 may also include a user interface 690 via which the wearer of the device may receive one or more recommendations or alerts generated either from a remote server or other remote computing device, or from a processor within the device. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, the user interface 690 may include a display 692 where a visual indication of the alert or recommendation may be displayed. The display 692 may further be configured to provide an indication of the measured physiological parameters, for instance, the concentrations of certain blood analytes being measured.

Other configurations are contemplated. For example, in other embodiments, the measurement platform and user interface may both be provided on the same side of the wearer's wrist, in particular, the anterior side of the wrist. On the posterior side, a watch face or digital display may be disposed on the strap.

C. Example Head-Mountable Device

In a further an example embodiment, the wearable device may take the form of or include a head-mountable device (HMD). Wearable computing devices with near-eye displays may also be referred to as "head-mountable displays" (HMDs), "head-mounted displays," "head-mounted devices," or "head-mountable devices." An HMD may generally be any display device that is capable of being worn on the head and places a display in front of one or both eyes of the wearer. Such displays may occupy a wearer's entire field of view, or occupy only a portion of a wearer's field of view. Further, head-mounted displays may vary in size, taking a smaller form such as a glasses-style display or a larger form such as a helmet or eyeglasses, for example. As such, references to "eyeglasses" or a "glasses-style" HMD should be understood to refer to an HMD that has a glasses-like frame so that it can be worn on the head. Further, example embodiments may be implemented by or in association with an HMD with a single display or with two displays, which may be referred to as a "monocular" HMD or a "binocular" HMD, respectively. To generate the images on a display, a computer processing system may be used.

Figure 7A:
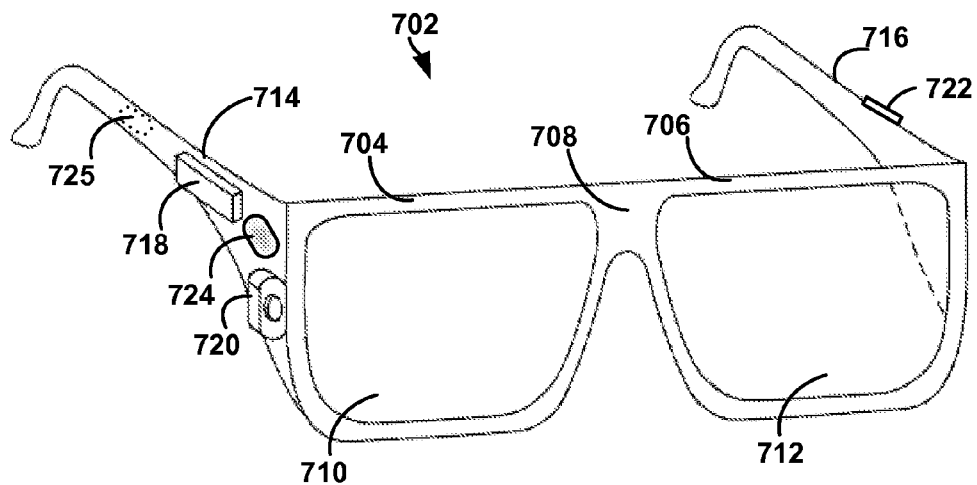
FIG. 7A illustrates an example head-mountable device, according to an example embodiment.

FIG. 7A illustrates one example of an HMD 702 (which may also be referred to as a head-mounted display). The HMD 702 includes frame elements including lens-frames 704, 706 and a center frame support 708, lens elements 710, 712, and extending side-arms 714, 716. The center frame support 708 and the extending side-arms 714, 716 are configured to secure the HMD 702 to a user's face via a user's nose and ears, respectively.

The HMD 702 may also include an on-board computing system 718, an image capture device 720, one or more sensors 722, and a finger-operable touch pad 724. The on-board computing system 718 is shown to be positioned on the extending side-arm 714 of the HMD 702; however, the on-board computing system 718 may be provided on other parts of the HMD 702 or may be positioned remote from the HMD 702 (e.g., the on-board computing system 718 could be wire- or wirelessly-connected to the HMD 702). The on-board computing system 718 may include a processor and memory, for example. The on-board computing system 718 may be configured to receive and analyze data from the one or more sensors 722, image capture device 720 and the finger-operable touch pad 724 (and possibly from other sensory devices, user interfaces, or both). Data collected by the computing system 718 may be used to generate images for output by the lens elements 710 and 712. HMD 702 may also include a wireless transceiver for communicating with a remote device, such as a positioning device 300.

The one or more sensors 722 are shown on the extending side-arm 716 of the HMD 702; however, the one or more sensors 722 may be positioned on other parts of the HMD 702, such as on an inner surface of side-arm 716. For illustrative purposes, only one sensor 722 is shown. However, in an example embodiment, the HMD 702 may include multiple sensors. For example, an HMD 702 may include sensors 702 such as one or more gyroscopes, one or more accelerometers, one or more magnetometers, one or more light sensors, one or more infrared sensors, one or more microphones and/or one or more sensors for sensing or measuring a physiological parameter. Other sensing devices may be included in addition or in the alternative to the sensors that are specifically identified herein.

Figure 7B:
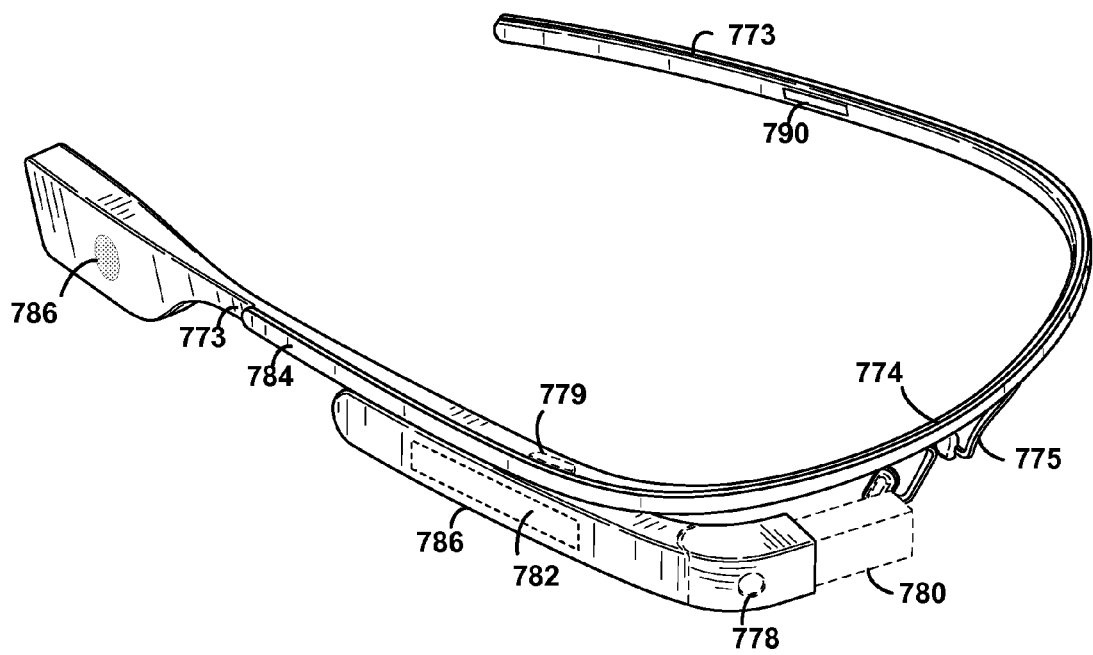
FIG. 7B illustrates another example head-mountable device, according to an example embodiment.

FIG. 7B illustrates another wearable computing system according to an example embodiment, which takes the form of a monocular HMD 772. The HMD 772 may include side-arms 773, a center frame support 774, and a bridge portion with nosepiece 775. In the example shown in FIG. 7B, the center frame support 774 connects the side-arms 773. The HMD 772 does not include lens-frames containing lens elements. The HMD 772 may additionally include a component housing 776, which may include an on-board computing system (not shown), an image capture device 778, and a button 779 for operating the image capture device 778 (and/or usable for other purposes). Component housing 776 may also include other electrical components and/or may be electrically connected to electrical components at other locations within or on the HMD. HMD 772 also includes a side-mounted touchpad 782 and a bone conduction transducer 786. One or more sensors 790, such as physiological parameter sensors, may also be provided on the HMD 772. In one example, the one or more sensors 790 are positioned on an inner surface of one or both of the side-arms 773 and, therefore, may be positioned against or in close proximity to the wearer's skin when the HMD 772 is worn.

The HMD 772 may include a single display 780, which may be coupled to one of the side-arms 773 via the component housing 776. In an example embodiment, the display 780 may be a see-through display, which is made of glass and/or another transparent or translucent material, such that the wearer can see their environment through the display 780. Further, the component housing 776 may include the light sources (not shown) for the display 780 and/or optical elements (not shown) to direct light from the light sources to the display 780. As such, display 780 may include optical features that direct light that is generated by such light sources towards the wearer's eye, when HMD 772 is being worn.

In a further aspect, HMD 772 may include a sliding feature 784, which may be used to adjust the length of the side-arms 173. Thus, sliding feature 784 may be used to adjust the fit of HMD 772. Further, an HMD may include other features that allow a wearer to adjust the fit of the HMD, without departing from the scope of the invention

D. Example Orally-Mountable Device

Figure 8A:
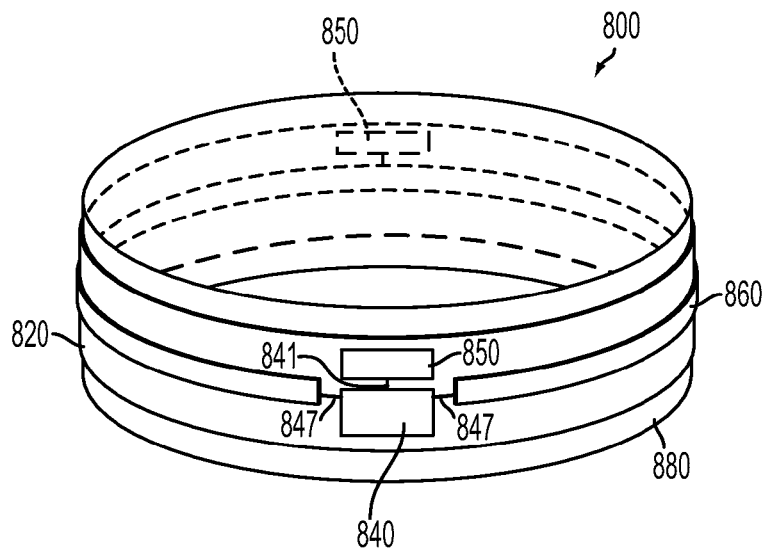
FIG. 8A illustrates an example orally-mountable device, according to an example embodiment.
Figure 8B:
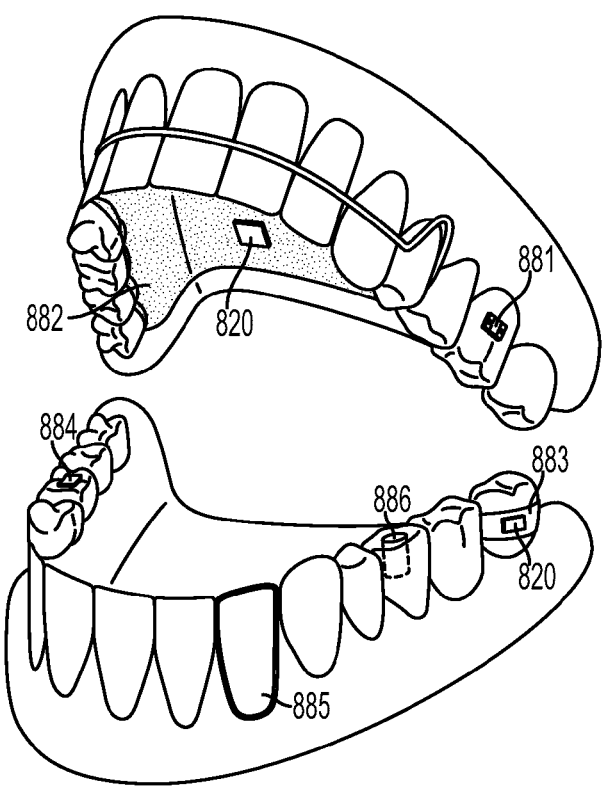
FIG. 8B illustrates several example orally-mountable devices, according to example embodiments.

Wearable device 200 may also be provided as one or more orally-mountable devices 800, as shown in FIGS. 8A and 8B. The oral device 800 may include a frame 880 and substrate 820 to provide a mounting surface for a power supply 830, a controller 840, sensor electronics 850, and a wireless transceiver, such as communication antenna 860. The sensor electronics 850 are operated by the controller 840. The power supply 830 supplies operating voltages to the controller 840 and/or the sensor electronics 850. The antenna 860 is operated by the controller 840 to communicate information to and/or from the oral device 800. The antenna 860, the controller 840, the power supply 830, and the sensor electronics 850 can all be situated on the embedded substrate 820.

Sensor electronics 850 may include one or more of an analyte sensor system, an activity sensor system and/or a volume sensor system. Additionally, sensor electronics can further include sensor(s) that measure light, temperature, blood pressure, pulse rate, respiration rate, air flow, and/or physiological parameters other than analyte concentration(s). Sensor electronics 850 can be situated the mounting surface of one or more substrates 820 or frames 880 within the mouth to detect and/or measure analyte concentrations in substances in the mouth, including food, drink and saliva. The substrates and/or frames and, in turn, one or more of the various sensors, can be mounted or positioned on or proximal to any number of surfaces within the mouth, including the teeth, gums, palate or tongue. Further, multiple substrates and/or frames and, in turn, multiple sensors, may be provided in a single device 800.

FIG. 8A illustrates one embodiment of an orally-mountable device 800, having a frame provided as a band 880, which can be mounted around a tooth, such as a molar. The band 880 may be made of stainless steel, titanium, ceramic, plastic or any other suitable material and may also be plated or coated with other materials, such as gold for wearers that are allergic to stainless steel. Similar to orthodontic applications, the band 880 may be provided in various sizes and shapes to accommodate the size, shape and positioning of the particular wearer's mouth and teeth. The diameter of band 880 may taper in the direction of the wearer's gum line to follow the curvature of a tooth and to hold the band 880 on the tooth with a friction fit. Biocompatible adhesives may also be used to affix band 880 to a tooth. The substrate 820, embedded in the band, can be shaped as a substantially flat ring or band with the substantially flat surface acting as a platform for mounting electronics such as chips (e.g., via flip-chip mounting) and for patterning conductive materials (e.g., via microfabrication techniques such as photolithography, deposition, plating, etc.) to form electrodes, antenna (e), and/or interconnections. In other examples, substrate 820 can be formed as one or more separate segments rather than as a single continuous substrate. For example, certain modules, such as a controller and a sensor, can be mounted to one substrate, while an antenna can be mounted to another substrate and the two can be electrically connected via interconnects.

Controller 840, sensor electronics 850, and a wireless transceiver, such as antenna 860, are disposed on the substrate 820. In some embodiments, antenna 860 may be provided as a loop antenna around the diameter of the frame 880. The controller 840 can be a chip including logic elements configured to operate the sensor electronics 850 and the loop antenna 860. The controller 840 is electrically connected to the loop antenna 860 by interconnects 847 also situated on the substrate 820. Similarly, the controller 840 is electrically connected to the sensor electronics 850 by an interconnect 841. The interconnects 841, 847, the loop antenna 860, and any conductive electrodes (e.g., for an electrochemical analyte bio-sensor, etc.) can be formed from conductive materials patterned on the substrate 820 by a process for precisely patterning such materials, such as deposition, photolithography, etc. The conductive materials patterned on the substrate 820 can be, for example, gold, platinum, palladium, titanium, carbon, aluminum, copper, silver, silver-chloride, conductors formed from noble materials, metals, combinations of these, etc.

Sensor electronics 850 may include one or more of an analyte sensor system, an activity sensor system and a volume sensor system (not shown). The analyte sensor system is configured to obtain sensor readings from the biological environment related to the presence or absence, and in some cases the concentration, of one or more target analytes. Analyte detection and measurement may be enabled through several possible mechanisms, including electrochemical reactions, change in impedance, voltage, or current etc. across a working electrode, and/or interaction with a targeted bioreceptor. In some examples, the analyte sensor system can include a multi-sensor array, each element of the array capable of sensing a different target analyte. For example, the device may comprise an array of enzyme or reagent sensors, such as those capable of sensing salivary amylase in connection with a starch substrate (which would indicate the conversion of starches to sugar), simple carbohydrates (sucrose, fructose, glucose), lipids, complex carbohydrates and ketone bodies (which may indicate ketoacidosis). The sensors may also include sensors for performing respiratory analyses, such as chemical noses for sensing ketones in the breath.

In some examples, the analyte sensor system may include one or more electrochemical sensors configured to cause an analyte to undergo an electrochemical reaction (e.g., a reduction and/or oxidation reaction) at a working electrode, one or more biosensors configured to detect an interaction of the target analyte with a bioreceptor sensitive to that analyte (such as proteins, enzymes, reagents, nucleic acids, phages, lectins, antibodies, aptamers, etc.), and one or more impedimetric biosensors configured to measure analyte concentrations at the surface of an electrode sensor by measuring change in impedance across the electrode, etc. Other detection and quantification systems and schemes are contemplated for implementation of the analyte sensor system.

The orally-mountable device 800 may additionally include an activity sensor system, configured to obtain activity sensor readings relating to the presence or absence of chewing activity in the mouth. The phrase "chewing activity" as used herein may be interpreted broadly to include any consuming activity, including eating, drinking, chewing, swallowing, etc. In essence, the activity sensor system is configured to determine if the wearer of the device is consuming a substance. Activity sensor system may include one or more optical sensors, pressure sensors and/or accelerometers, to determine if the user is eating, chewing or drinking Activity sensor readings may be obtained by the reader and used in conjunction with the analyte sensor readings to provide an indication of the health state of the wearer of the device or determine if the wearer is experiencing a medical condition.

In addition, the orally-mountable device 800 may include a volume sensor system to make volumetric measurements, for example, the size of a "bite" or amount of food, drink or other substance present in a person's mouth. The volume sensor system may include one or more sensors placed on one or more teeth within the wearer's mouth in a predetermined configuration. Sensors may include stress, pressure, tension sensors or the like for detecting a physical force acting on the sensors by the food or other substance in the mouth when the wearer chews. In other examples, the volume sensor system may include optical, acoustic or other types of sensors for sensing the angle of opening of the jaws or the distance between certain teeth during chewing activities which may provide an indication of the size of a bite of food taken by the wearer of the device.

Sensor electronics 850 may be provided on an outer-facing surface of substrate 820 so as to readily come into contact with saliva, food, drink and other substances within the mouth. In some examples, sensor electronics 850 may be provided on an inner surface of substrate 820 and/or frame 880 and may be configured to sense analyte concentrations in saliva, food, drink, etc. through a channel (not shown) passing from the outer-facing to the inner-facing surface of the substrate 820. In some embodiments, some electronic components can be mounted on one side of the substrate 820, while other electronic components are mounted to the opposing side, and connections between the two can be made through conductive materials passing through the substrate 820. Further, as shown in FIG. 8A, sensor electronics 850 may be provided on one or both of the buccal (cheek-facing) and lingual (tongue facing) or palatal (palate facing) sides of a tooth.

FIG. 3B illustrates various embodiments of a frame 880 for use with device 800. In some examples, one or more orally-mountable devices 800 may be used and may include additional frames and or substrates mounted to other teeth or located at different positions within the mouth. Frame 880 can be provided as or integrated in various orthodontic devices, such as one or more brackets 881 (such as those used in braces), a retainer 882, or a ring or band 883 placed around a tooth. In the case of a retainer frame 882, various sensor systems may be integrated onto the single frame, including sensors on or embedded in the roof portion of the retainer, sensors held against the inner or outer surfaces of the teeth by wire portions of the retainer, and/or sensors held against the chewing surfaces of the teeth, all electrically connected on a single platform. Various dental devices or methods may also be used to secure or mount one or more sensors within the mouth, including dental fillings 884, veneers 885, dental implants 886 or thin films on any surface of the tooth. Sensors may also be mounted to or implanted in the tissues within the mouth, such as the tongue, palate, or gums. Accordingly, the size and shape of frame 880 may be chosen to correspond to the shapes and curvatures of the chosen oral surface, i.e., the roof of the mouth, the inner or chewing surface of a tooth, etc. and the particular size and/or shape of the wearer's mouth.

The terms "oral device" or "orally mountable device," as used in this disclosure, refer to any device that is capable of being mounted, affixed, implanted or otherwise worn in the mouth, such as on, in or in proximity to a tooth, the tongue, a cheek, the palate, the lips, the upper or lower jaw, the gums, or other surface in the mouth. For example, the device 100 can be realized in a plurality of forms including, but not limited to, a crown, a retainer, dentures, orthodontic braces, dental implant, intra-tooth device, veneer, intradental device, mucosal implant, sublingual implant, gingivae implant, frenulum implant, or the like.

V. Illustrative Methods for Real-Time, High-Density Physiological Data Collection Using a Wrist Mounted Device A method for using a wearable device to take real-time, high-density measurements of physiological parameters is also provided. In a first step, the wearable device measures one or more physiological parameters during each of a plurality of measurement periods. The length of the measurement period may be set on the device itself or may be set remotely, for example, by instruction from a remote server. The device may be configured with many measurement periods each day—for example, continuous, every second, every minute, every hour, every 6 hours, etc.—or may be configured to take measurements once a week or once a month. Further, a different measurement period may be set for each of the physiological parameters being measured. The measurement periods may extend through a plurality of consecutive days and each of the consecutive days may include multiple measurement periods. Each of the consecutive days may further include at least twenty-four measurement periods and the plurality of consecutive days may include at least thirty days. At least some of the physiological parameters are measured by non-invasively detecting one or more analytes in blood circulating in subsurface vasculature proximate to the wearable device.

After conclusion of a measurement period, for each of the plurality of measurement periods, the wearable device transmits to a server, or remote device, data representative of the physiological parameters measured during that measurement period. The wearable device may be configured to automatically transmit the data to a server, may be configured to transmit on command of the wearer, or may be configured to transmit on instruction from a remote server. Further, the device may be configured to automatically transmit the data at the end of each measurement period, or at some more frequent or infrequent rate. For example, the device could be configured to transmit every five minutes, at the end of each day, at the end of the month, at nighttime only, etc.

In response, the server, or remote computing device, is configured to develop a baseline profile based on the data transmitted by the wearable device for the plurality of measurement periods. In some embodiments, the baseline profile includes an individual baseline profile based on the data transmitted by the wearable device for the plurality of measurement periods for an individual user wearing the wearable device. The baseline profile may include patterns for how one or more of the wearer's physiological parameters typically change over time, such as during the course of a day, a week, or a month. The baseline profile may further include threshold values of certain target analytes, above or below which a medical condition may be indicated.

After the server has developed an individual baseline profile for a wearer of the device, the server may receive additional data regarding the physiological parameters from the wearable device measured during one or more additional measurement periods. The server may then compare the additional data, collected over additional measurement periods, to the individual baseline profile. If the additional data is consistent with the patterns embodied in the individual baseline profile, the server may determine that the wearer's condition has not changed. On the other hand, if the additional data deviates from the patterns embodied in the baseline profile, the server may detect a change in the wearer's condition. The change in condition could, for example, indicate that the wearer has developed a disease, disorder, or other adverse medical condition or may be at risk for a severe medical condition, such as a stroke or a heart attack, in the near future.

If the server detects a change in condition based on the individual baseline profile and the additional data, it may generate one or more recommendations based on the detected change in condition and a clinical protocol. For example, the server may generate a recommendation that the wearer take a particular medication or supplement, schedule an appointment with a medical professional, go to the hospital to seek immediate medical attention, abstain from certain activities, etc. The server may also be configured to receive data regarding physiological parameters measured by a plurality of wearable devices and use that data to develop, at least in part, the clinical protocol. The clinical protocol may also be developed based, at least in part, on any known health information or medical history of the wearer, and/or on recognized standards of care in the medical field. The wearable device may receive the one or more recommendations generated by the server and providing an indication of the one or more recommendations via a user interface on the wearable device.

In some embodiments, the server may be configured to receive data regarding physiological parameters measured by a plurality of wearable devices. The server may use this data collected from a plurality of wearable devices—worn by a plurality of users—to develop, at least in part, a population baseline profile. Such population baseline profiles may be used, for example, for comparison with an individual's baseline profile. Those of skill in the art will readily recognize that comparison of an individual's physiological parameters measured over time to that individual's own baseline may not be sufficient to recognize an abnormality in that physiological parameter. For example, while a physiological parameter for an individual wearer of the device may not deviate from that individual's baseline, that individual baseline may be well above the population baseline generated from data collected from a plurality of wearers of the device. Thus, comparison to what is "normal" or "average" for a population may be necessary for effective identification or prevention of a medical condition in an individual.

Accordingly, the server may further be configured to receive from the wearable device additional data measured during one or more additional measurement periods, detect a change in condition based on the population baseline profile and the additional data, and generate one or more recommendations based on the detected change in condition and a clinical protocol. The wearable device may receive the one or more recommendations generated by the server and provide an indication of the one or more recommendations via a user interface on the wearable device.

In a further example, the server may be configured to receive data regarding physiological parameters measured by a plurality of wearable devices and receive an indication of the health state of the users of the plurality of wearable devices for a plurality of measurement periods. The server may then derive a correlation between the health state of the users and the data representative of the physiological parameters measured during the plurality of measurement periods. Population data of this kind may be significant in that such correlations may never before have been drawn between that physiological parameter and a particular health condition. Such correlations may be used in prediction, prevention, diagnoses and treatment of health conditions. The server may also be configured to receive from the wearable device additional data representative of the physiological parameters measured during one or more additional measurement periods and generate one or more recommendations based on the received additional data and a clinical protocol, wherein the clinical protocol is developed based, at least in part, on the derived correlation.

In a further example, the wearable device itself may be configured to perform the steps described above as being performed by a remote server. For example, the wearable device may be configured to analyze the data representative of the physiological parameters, generate a baseline profile, compare data collected from additional measurement periods to the baseline profile, and generate recommendations based on a clinical protocol. The wearable device may further be configured to transmit, either automatically or on some other frequency, certain data to the remote server.

It will be readily understood that the aspects of the present disclosure, as generally described herein, and illustrated in the figures, can be arranged, substituted, combined, separated, and designed in a wide variety of different configurations, all of which are explicitly contemplated herein. While various aspects and embodiments have been disclosed herein, other aspects and embodiments will be apparent to those skilled in the art.

Example methods and systems are described above. It should be understood that the words "example" and "exemplary" are used herein to mean "serving as an example, instance, or illustration." Any embodiment or feature described herein as being an "example" or "exemplary" is not necessarily to be construed as preferred or advantageous over other embodiments or features. Reference is made herein to the accompanying figures, which form a part thereof. In the figures, similar symbols typically identify similar components, unless context dictates otherwise. Other embodiments may be utilized, and other changes may be made, without departing from the spirit or scope of the subject matter presented herein. The various aspects and embodiments disclosed herein are for purposes of illustration and are not intended to be limiting, with the true scope and spirit being indicated by the following claims.

What is claimed is:

1. A method comprising:
   receiving, by a wearable device, a location signal from a positioning device having location-determining capabilities indicative of a location of the positioning device, wherein the wearable device includes at least one sensor configured to measure at least one physiological parameter;
   calculating, a first location of the wearable device based, at least in part, on the location of the positioning device and a strength of the location signal received by the wearable device;
   in response to loss of the location signal at the wearable device after calculating the first location of the wearable device:
      storing, on the wearable device, the first location of the wearable device; and
      storing, on the wearable device, wearable device movement data received from one or more movement sensors located on the wearable device and a timestamp associated with the wearable device movement data, wherein the wearable device movement data is indicative of movement of the wearable device; and
   in response to reestablishing the location signal at the wearable device:
      receiving, by the wearable device, an updated location signal from the positioning device and a timestamp associated with the updated location signal, wherein the updated location signal is indicative of one or more updated locations of the positioning device;

correlating the wearable device movement data and the updated location signal based, at least in part, on their associated timestamps; and calculating an updated location of the wearable device based, at least in part, on the wearable device movement data correlated with the updated location signal, a strength of the updated location signal received by the wearable device, and the first location of the wearable device.

2. The method of claim 1, wherein the first location of the wearable device is further calculated based, at least in part, on a direction of the location signal received by the wearable device.

3. The method of claim 1, wherein the one or more movement sensors on the wearable device comprise one or more of a compass, an accelerometer, an inertial measurement unit, an altitude meter, and a gyroscope.

4. The method of claim 1, wherein the wearable device movement data includes one or more of direction, altitude, speed, and acceleration.

5. The method of claim 1, wherein the updated location of the wearable device is further calculated based, at least in part, on positioning device movement data received from the positioning device indicative of movement of the positioning device.

6. The method of claim 1, further comprising detecting, by the wearable device, whether the wearable device is within range of the positioning device.

7. A wearable device, comprising:
a wireless transceiver;
at least one sensor configured to measure at least one physiological parameter;
a processor; and
a non-transitory computer readable medium storing instructions thereon that, when executed by the processor, cause the wearable device to perform functions, the functions comprising:
  receiving, by the wireless transceiver, a location signal from a positioning device having location determining capabilities indicative of a location of the positioning device;
  calculating a first location of the wearable device based, at least in part, on the location of the positioning device and a strength of the location signal received by the wearable device;
  in response to loss of the location signal at the wearable device after calculating the first location of the wearable device:
    storing, on the wearable device, the first location of the wearable device; and
    storing, on the wearable device, wearable device movement data received from one or more movement sensors located on the wearable device and a timestamp associated with the wearable device movement data, wherein the wearable device movement data is indicative of movement of the wearable device; and
  in response to reestablishing the location signal at the wearable device:
    receiving, by the wearable device an updated location signal from the positioning device and a timestamp associated with the updated location signal, wherein the updated location signal is indicative of one or more updated locations of the positioning device;
    correlating the wearable device movement data and the updated location signal based, at least in part, on their associated timestamps; and
    calculating an updated location of the wearable device based, at least in part, on the wearable device movement data correlated with the updated location signal, a strength of the updated location signal received by the wearable device, and the first location of the wearable device.

8. The wearable device of claim 7, wherein the first location of the wearable device is further calculated based, at least in part, on a direction of the location signal received by the wearable device.

9. The wearable device of claim 7 wherein the one or more motion sensors on the wearable device comprise one or more of a compass, an accelerometer, an inertial measurement unit, an altitude meter and a gyroscope.

10. The method of claim 7, wherein the wearable device movement data includes one or more of direction, altitude, speed, and acceleration.

11. The wearable device of claim 7, wherein the wireless transceiver is configured to communicate using a wireless protocol comprising one of: a Radio-Frequency Identification (RFID) protocol, a Bluetooth protocol, a Wi-Fi protocol and a Zigbee protocol.

12. The wearable device of claim 7, wherein functions further comprise detecting whether the wearable device is within range of the positioning device.

* * * * *